(12) United States Patent
Mais et al.

(10) Patent No.: US 8,501,945 B2
(45) Date of Patent: *Aug. 6, 2013

(54) PROCESS FOR PREPARING METHYL {4,6-DIAMINO-2-[1-(2-FLUOROBENZYL)-1H-PYRAZOLO[3,4-B]PYRIDIN-3-YL] PYRIMIDIN-5-YL}CARBAMATE AND ITS PURIFICATION FOR USE AS PHARMACEUTICALLY ACTIVE COMPOUND

(75) Inventors: Franz-Josef Mais, Düsseldorf (DE);
Joachim Rehse, Leichlingen (DE);
Winfried Joentgen, Köln (DE); Konrad Siegel, Düsseldorf (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 145 days.

This patent is subject to a terminal disclaimer.

(21) Appl. No.: 12/955,864

(22) Filed: Nov. 29, 2010

(65) Prior Publication Data

US 2011/0130411 A1 Jun. 2, 2011

(30) Foreign Application Priority Data

Nov. 27, 2009 (EP) .................................. 09177369

(51) Int. Cl.
C07D 403/04 (2006.01)
A61K 31/506 (2006.01)
A61P 19/02 (2006.01)

(52) U.S. Cl.
USPC .......................................... 544/328; 514/256

(58) Field of Classification Search
USPC .................. 544/328; 514/256, 328
See application file for complete search history.

(56) References Cited

U.S. PATENT DOCUMENTS

| | | | |
|---|---|---|---|
| 6,833,364 B1 | 12/2004 | Straub et al. | |
| 6,903,089 B1 | 6/2005 | Stasch et al. | |
| 6,919,345 B2 | 7/2005 | Stasch et al. | |
| 7,115,599 B2 | 10/2006 | Stasch et al. | |
| 7,173,037 B2 | 2/2007 | Alonso-Alija et al. | |
| 2004/0235863 A1 | 11/2004 | Feurer et al. | |
| 2005/0222170 A1 | 10/2005 | Welgand et al. | |
| 2007/0225299 A1 | 9/2007 | Bischoff et al. | |
| 2010/0029653 A1 | 2/2010 | Schirok et al. | |
| 2010/0113507 A1 | 5/2010 | Furstner et al. | |
| 2012/0029002 A1 | 2/2012 | Straub et al. | |

FOREIGN PATENT DOCUMENTS

| CA | 2339071 A1 | 2/2000 |
|---|---|---|
| CA | 2346698 A1 | 4/2000 |
| CA | 2429309 A1 | 5/2002 |
| CA | 2429313 A1 | 5/2002 |
| CA | 2309332 A1 | 12/2002 |
| CA | 2544621 A1 | 5/2005 |
| CA | 2268314 A1 | 12/2006 |
| CA | 2272584 A1 | 10/2007 |
| CA | 2268394 A1 | 3/2008 |
| CA | 2429308 A1 | 9/2010 |
| CA | 2429312 A1 | 1/2011 |
| CA | 2485143 A1 | 4/2011 |
| EP | 0463756 B1 | 4/1995 |
| WO | 9428902 A1 | 12/1994 |
| WO | 9519978 A1 | 7/1995 |
| WO | 0006567 A1 | 2/2000 |
| WO | 0006568 A1 | 2/2000 |
| WO | 2010079120 A1 | 7/2010 |

OTHER PUBLICATIONS

Mittendorf et al., "Discovery of Riociguat (BAY 63/2521): A Potent, Oral Stimulator of Soluble Guanylate Cyclase for the Treatment of Pulmonary Hypertension," Chem Med Chem, No. 4, 853-865 (2009).

Ko et al., "YC-1, a Novel Activator of Platelet Guanylate Cyclase;" Blood, 84, pp. 4226-4233 (1994).

Mulsch et al., "Effect of YC-1, an NO-independent, Superoxide-Sensitive Stimulaotr of Soluble Gyanylyl Cyclase, on Smooth Muscle Responsiveness to Nitrovasodilators;" Brit. J. Pharm., 120, pp. 681-689 (1997).

(Continued)

*Primary Examiner* — Venkataraman Balasubramanian
(74) *Attorney, Agent, or Firm* — Karen B. King

(57) ABSTRACT

The present invention relates to processes for preparing methyl {4,6-diamino-2-[1-(2-fluorobenzyl)-1H-pyrazolo[3,4-b]pyridin-3-yl]pyrimidin-5-yl}carbamate, i.e. the compound of the formula (I)

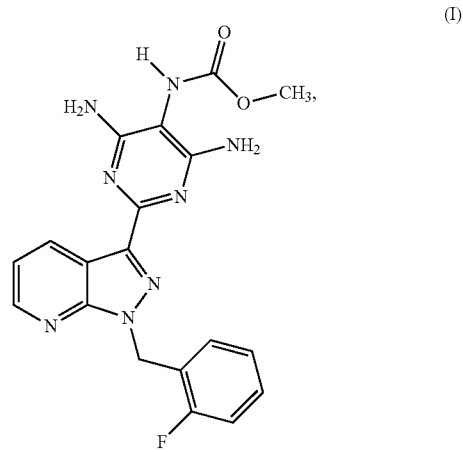

and to a process for purifying the crude product of the formula (I) for use as pharmaceutically active compound, where, for purification, methyl {4,6-diamino-2-[1-(2-fluorobenzyl)-1H-pyrazolo[3,4-b]pyridin-3-yl]pyrimidin-5-yl}carbamate sulphinyldimethane (1:2) of the formula (II) is isolated as intermediate or is generated as intermediate in this purification process, if appropriate present in a mixture.

2 Claims, No Drawings

(56) References Cited

OTHER PUBLICATIONS

Goldberg et al., "Stimulation of Human Platelet Guanylate Cyclase by Fatty Acids," J. Biol. Chem., 252, pp. 1279-1285 (1977).

Pettibone et al., "A Structurally Novel Stimulator of Guanylate Cyclase with Long-Lasting Hypotensive Activity in the Dog," Euro. J. of Pharmacology, 116, pp. 307-312 (1985).

Yu et al., "Vasorelaxant Effect of Isoliquiritigenin, A Novel Soluble Guanylate Cyclase Activator, in Rat Aorta," Brit. J. of Pharmacology, 114, pp. 1587-1594 (1995).

Cavalieri et al., "A Synthesis of Adenine: The Incorporation of Isotopes of Nitrogen and Carbon," J. Am. Chem. Soc., 71, pp. 533-536 (1949).

Barraclough et al., "Mono-aroylation of 2,3-and 3,4-Diaminopyridine and 4,5-Diaminopyrimidine, and Syntheses of Putative Inotrope/b-Adrenoceptor Antagonists," J. Chem. Res., vol. 9, 2316-2335 (1996).

Li et al., "Synthesis and Structure-Activity Relationships of 2-Pyridones: A Novel Series of Potent DNA Gyrase Inhibitors as Antibacterial Agents," J. Med. Chem. 39, pp. 3070-3088 (1996).

Evans et al.: "The Preparation of 4-Amino-and Other Pteridines," J. of Chem. Soc. pp. 4106-4113 (1956).

Schwoch et al. "2-3-Dihydrospirol [1H-4 and 5-azabenzimidazole-2,1'-cyclohexane](=Spiro[cyclohexane-1.2'(3'H)-imidazo[4,5-hb]pyridine] and Spiro[cyclohexane-1.2'(3'H)-1H-imidaxo[4,5-c[pyridine]): Reactions with Nucleophiles," Helvetia Chimica Acta, vol. 77, pp. 2175-2190 (1994).

Machine English translation of text of WO 2010/079120, generated by the online translator on http: www.espacenet. com, Jul. 11, 2010.

An English equivalent WO 2000/06567, as filed at US national stage, U.S. Appl. No. 09/744,704 (unpublished), Feb. 10, 2000.

U.S. Appl. No. 12/955,864, filed Oct. 29, 2010.

U.S. Appl. No. 13/111,856, filed May 19, 2011.

PROCESS FOR PREPARING METHYL {4,6-DIAMINO-2-[1-(2-FLUOROBENZYL)-1H-PYRAZOLO[3,4-B]PYRIDIN-3-YL]PYRIMIDIN-5-YL}CARBAMATE AND ITS PURIFICATION FOR USE AS PHARMACEUTICALLY ACTIVE COMPOUND

The present invention relates to processes for preparing methyl {4,6-diamino-2-[1-(2-fluorobenzyl)-1H-pyrazolo[3,4-b]pyridin-3-yl]pyrimidin-5-yl}carbamate, i.e. the compound of the formula (I)

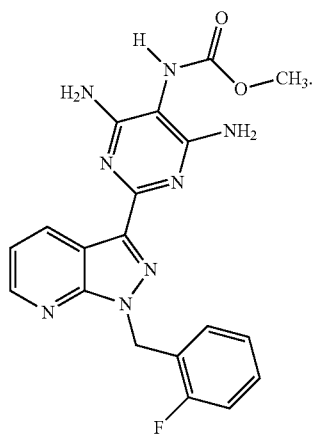

(I)

The invention furthermore relates to a process for purifying the crude product of the formula (I) for use as a pharmaceutically active compound, where, for purification, methyl {4,6-diamino-2-[1-(2-fluorobenzyl)-1H-pyrazolo[3,4-b]pyridin-3-yl]pyrimidin-5-yl}carbamate sulphinyldimethane (1:2), i.e. a compound of the formula (II) is isolated as intermediate or is generated as intermediate in this purification process, if appropriate present in a mixture

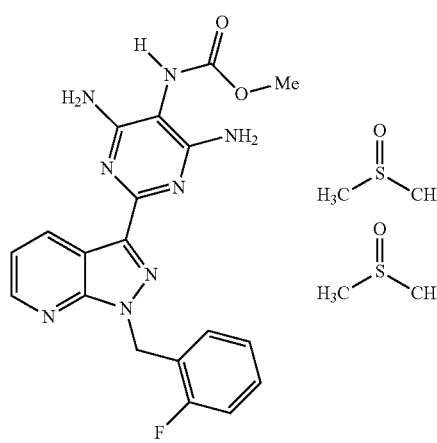

(II)

The compound of the formula (I) acts as a stimulator of soluble guanylate cyclase and can be used as an agent for the prophylaxis and/or treatment of cardiovascular disorders such as, for example, for the treatment of high blood pressure and of heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenoses such as following thrombolysis therapies, percutaneous transluminal angioplasties (PTA), percutaneous transluminal coronary angioplasties (PTCA), bypass and for the treatment of arteriosclerosis, asthmatic disorders and diseases of the urogenital system such as, for example, prostate hypertrophy, erectile dysfunction, female sexual dysfunction, osteoporosis, glaucoma, pulmonary hypertension, gastroparesis and incontinence.

The preparation of the compound of the formula (I) and its purification are known in principle. WO 03/095451 describes the preparation of the compound of the formula (I) by the route below.

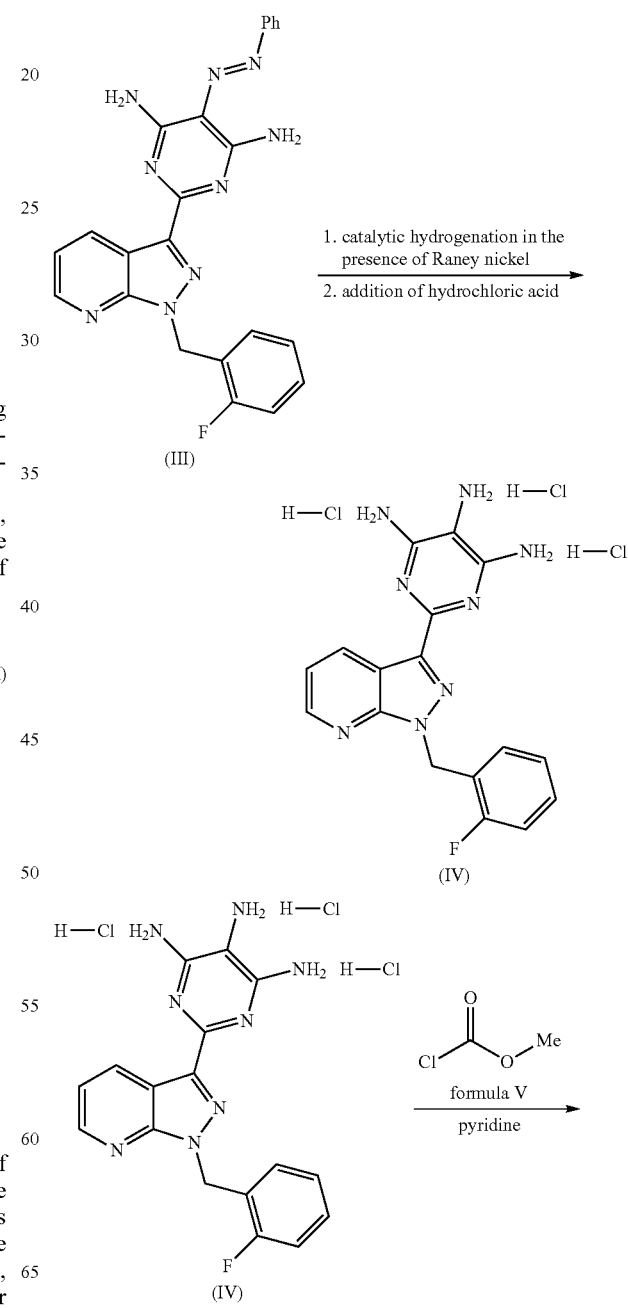

-continued

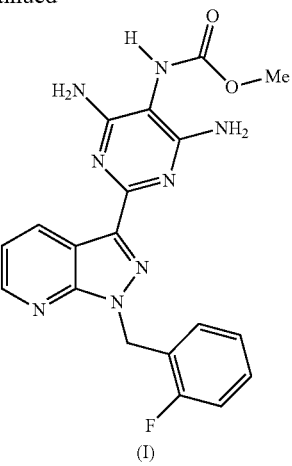

(I)

Here, initially 2-[1-(2-fluorobenzyl)-1H-pyrazolo[3,4-b]pyridin-3-yl]-5-[(E)-phenyldiazenyl]-pyrimidine-4,6-diamine of the formula (III) is cleaved by catalytic hydrogenation, and the resulting trisamino compound is isolated as 2-[1-(2-fluorobenzyl)-1H-pyrazolo[3,4-b]pyridin-3-yl]-4,5,6-pyrimidinetriamine trihydrochloride of the formula (IV). This trihydrochloride is then reacted with methyl chloroformate of the formula (V) in the solvent pyridine to give methyl 4,6-diamino-2-[1-(2-fluorobenzyl)-1H-pyrazolo[3,4-b]pyridin-3-yl]-5-pyrimidinylcarbamate of the formula (I). Alternatively, ChemMedChem 2009, 4, 853-865 describes that the trisamino compound is isolated as trihydrochloride and the HCl-free base is then generated by extraction with aqueous NaHCO₃ solution and the free base is reacted with the methyl chloroformate of the formula (V) in the solvent pyridine to give the compound of the formula (I).

This synthesis has a number of disadvantages which are very unfavourable for an industrial realization on a large scale. This is true especially for the isolation of the trisamino compound as trihydrochloride. The addition of hydrochloric acid requires an acid-proof industrial plant, and the yield of the step is only an unsatisfactory 59.3% of theory (see Example 8A of WO 03/095451). The realization of the reaction of the trisamino compound of the formula (IV) or the corresponding HCl-free base in the solvent pyridine is likewise disadvantageous. The compound of the formula (I) can only be isolated by complete evaporation of the reaction mixture, which is disadvantageous on an industrial scale (see, for example, Example 5 of WO 03/095451). On a relatively large scale, such steps generally result in considerable problems such as sticking-on or thermal decomposition owing to the substantially longer thermal stress when a reaction is carried out on a relatively large scale. The fact that the product is purified, for example according to Example 5 from WO 03/095451 by boiling in diethyl ether, too, has considerable disadvantages. Because of the high flammability of diethyl ether, this step can be realized only with increased industrial expenditure. However, particularly disadvantageous is the fact that the substance of the formula (I) which was prepared according to WO 03/095451 still contains a number of impurities in amounts which conflict with use as a pharmaceutically active compound.

Accordingly, it was the object to provide a simplified process which is safe and can also be carried out on an industrial scale and at the same time affords an active compound in extremely high purity in pharmaceutically acceptable quality.

We have now found a process for preparing methyl {4,6-diamino-2-[1-(2-fluorobenzyl)-1H-pyrazolo[3,4-b]pyridin-3-yl]pyrimidin-5-yl}carbamate of the formula (I)

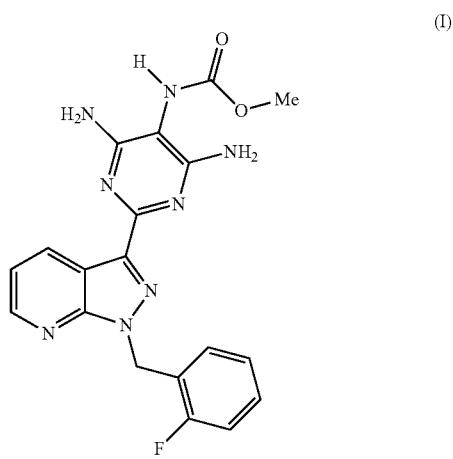 [SMILES: COC(=O)Nc1c(N)nc(-c2nn(Cc3ccccc3F)c3ncccc23)nc1N]

(I)

and its purification for use as a pharmaceutically active compound.

This novel process differs from the processes known to date in the following points:

After catalytic hydrogenation of the compound of the formula (III), the trisamino compound is isolated as the free base of the formula (VI), i.e. the free base of the compound of the formula (IV) without intermediate formation of salts

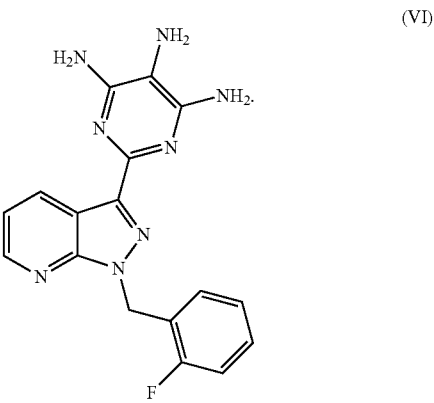 [SMILES: Nc1nc(-c2nn(Cc3ccccc3F)c3ncccc23)nc(N)c1N]

(VI)

The preparation of the compound of the formula (I) is carried out using methyl chloroformate or dimethyl dicarbonate as reagent in a pyridine-free process.

The purification of the crude product of the formula (I) for use as pharmaceutically active compound is carried out via the compound methyl {4,6-diamino-2-[1-(2-fluorobenzyl)-1H-pyrazolo[3,4-b]pyridin-3-yl]pyrimidin-5-yl}carbamate sulphinyldimethane (1:2), i.e. a compound of the formula (II) as isolated intermediate or generated in a mixture

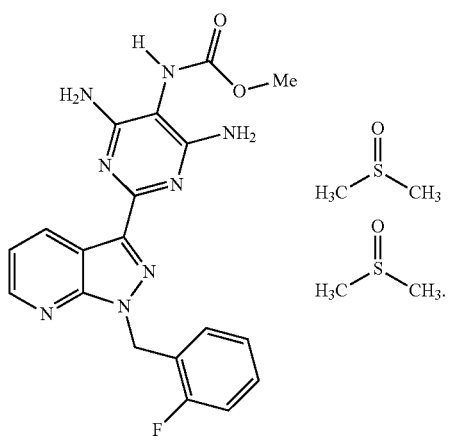

(II)

By virtue of these differences, it is possible to overcome the disadvantages of the processes known to date and to obtain an active compound in high yield and high purity and pharmaceutically acceptable quality.

The process according to the invention for preparing the compound of the formula (I) and the purification via the intermediate of the formula (II) are described in detail below.

Catalytic Hydrogenation of the Compound of the Formula (III)

The process according to the invention begins with a catalytic hydrogenation of the compound of the formula (III).

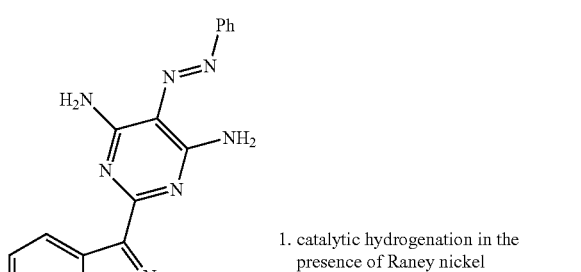

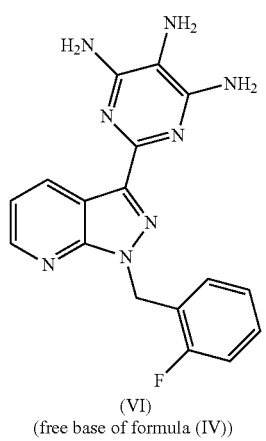

(VI)
(free base of formula (IV))

This may be carried out in the presence of Raney nickel or industrially customary Pt/carbon or Pd/carbon catalysts. Preference is given to Pt/carbon and Pd/carbon. N,N-Dimethylformamide (DMF), N,N-dimethylacetamide (DMA) or N-methyl-2-pyrrolidone (NMP), preferably DMF, serves as solvent.

Hydrogenation conditions are temperature 40-80° C., preferably 50-70° C., pressure: 2-90 bar, preferably 5-70 bar, of hydrogen, hydrogenation time: 1-72 h, preferably 3-36 h.

After removal of the catalyst by filtration, the product is precipitated with $C_1$-$C_4$-alcohol, preferably methanol or ethanol, and/or water. Preference is given to the mixture of methanol or ethanol and water.

In the context of the invention, a $C_1$-$C_4$-alcohol is a straight-chain or branched alcohol having 1 to 4 carbon atoms. The following may be mentioned by way of example and by way of preference: methanol, ethanol, n-propanol, isopropanol, n-butanol and tert-butanol. This definition also applies to the $C_1$-$C_4$-alcohols used hereinbelow.

It is also possible to remove some of the solvent used for the hydrogenation prior to the precipitation; a partial distillative removal of 0-80%, preferably 40-70%, of the solvent present prior to the addition of the precipitation solvent or solvents is in accordance with the invention. It is preferred according to the invention to distil off some of the solvent prior to the addition of the precipitation solvents.

The moist product obtained in this manner is dried in a customary manner under reduced pressure: this gives the product of the formula (VI) (corresponds to the free base of the formula (IV)).

Reaction of the Compound of the Formula (VI) with Methyl Chloroformate (V)

The product of the formula (VI) is then reacted, for example, with methyl chloroformate of the formula (V) in a novel pyridine-free process to give the crude product of the formula (I).

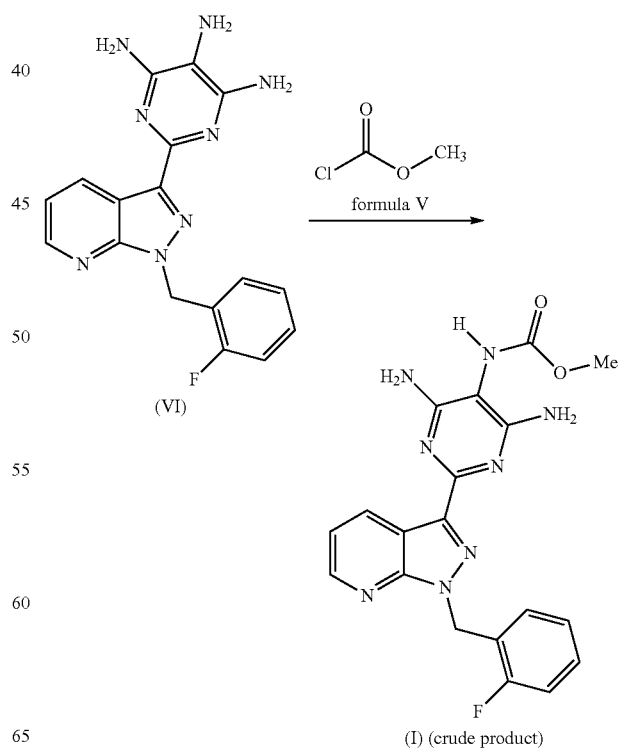

The solvents used for the reaction are $C_1$-$C_4$-alcohols, preferably ethanol, methanol, isopropanol, particularly preferably isopropanol.

The amount of methyl chloroformate is from 1.0 to 3.0 equivalents, preferably from 1.0 to 2.0 equivalents, based on the compound of the formula (VI) employed.

Possible reaction temperatures are 0-75° C., preferably 15-50° C.

During the reaction, hydrogen chloride is formed which forms a compound of the formula (VII), i.e. the hydrochloride of the product of the formula (I), in the reaction mixture. This hydrochloride of the formula (VII) can either be isolated as HCl-containing product and be cleaved by addition of base to the crude product of the formula (I), or it can be cleaved by addition of base even before the isolation, so that the crude product of the formula (I) is isolated directly.

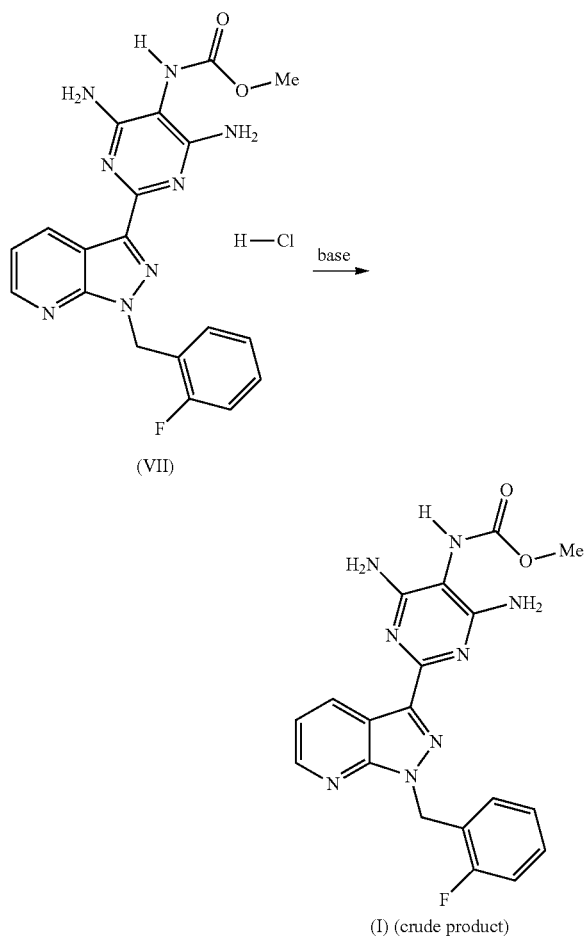

According to the invention, it is preferred to cleave the product of the formula (VII) by addition of the base prior to the isolation and to isolate the crude product of the formula (I) directly.

According to the invention, suitable bases are all bases having a pKB which is higher than that of the compound of the formula (I). Examples which may be mentioned are: hydroxides, carbonates and phosphates of the alkali metals and alkaline earth metals, nitrogen-containing organic bases, such as trialkylamines, guanidines or amidines. Examples which may be mentioned are: lithium hydroxide, sodium hydroxide, potassium hydroxide, rubidium hydroxide, caesium hydroxide, magnesium hydroxide, calcium hydroxide, strontium hydroxide, barium hydroxide, lithium carbonate, sodium carbonate, potassium carbonate, rubidium carbonate, caesium carbonate, magnesium carbonate, calcium carbonate, strontium carbonate and barium carbonate, sodium phosphate and potassium phosphate, trialkylamines having straight-chain, cyclic or branched $C_1$-$C_{20}$-alkyl radicals, and cyclic or open-chain guanidines or amidines. Preference according to the invention is given to triethylamine, tripropylamine, diisopropylethylamine, tributylamine, dicyclohexylethylamine, cyclohexyldimethylamine, cyclohexyldiethylamine, triisooctylamine, tridecylamine, tridodecylamine, trihexadecylamine, N-methylmorpholine, DBU, DBN, tetramethylguanidine, etc. Particular preference is given to triethylamine, tributylamine, N-methylmorpholine, diisopropylethylamine, DBU, DBN.

The solvents used for the cleavage are $C_1$-$C_4$-alcohols, preferably ethanol, methanol, isopropanol, particularly preferably isopropanol. Mixtures of the abovementioned solvents, e.g. isopropanol and methanol, are also used particularly preferably.

The amount of base is from 1.0 to 2.0 equivalents, preferably from 1.0 to 1.5 equivalents, based on the methyl chloroformate of the formula (V) employed.

Possible reaction temperatures for the reaction with the base are 0-100° C., preferably 15-70° C.

The crude product of the formula (I) is present in suspension and is isolated by filtration. It is washed with the $C_1$-$C_4$-alcohol and dried under reduced pressure in a customary manner.

It is possible to dry the hydrochloride of the formula (VII) in the intermediate isolation and then to carry out the reaction with the base to give the crude product of the formula (I). However, it is preferred according to the invention not to dry the product of the formula (VII) but rather to carry out the reaction with the base directly to give the crude product of the formula (I).

Reaction of the Compound of the Formula (VI) with Dimethyl Dicarbonate (VIII)

In a further process according to the invention, the product of the formula (VI) is reacted with dimethyl dicarbonate of the formula (VIII) to give the crude product of the formula (I). This reaction does not require any base such as, for example, pyridine.

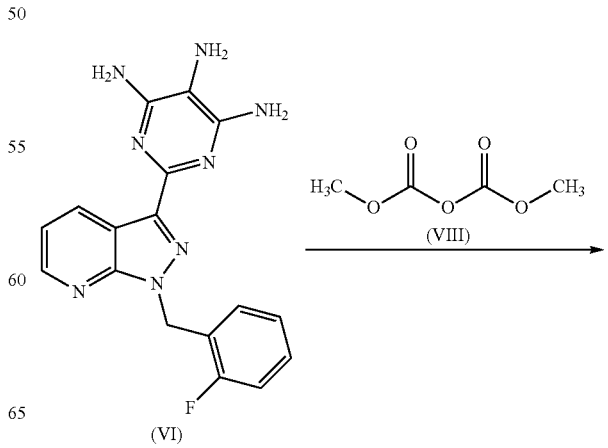

-continued

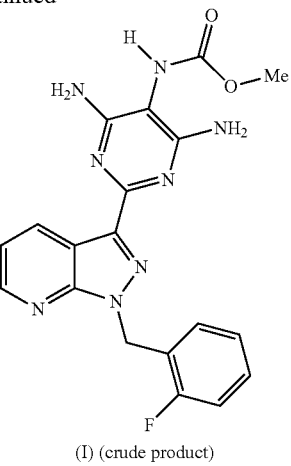

(I) (crude product)

The solvents used for this reaction are $C_1$-$C_4$-alcohols, preferably ethanol, methanol, isopropanol, particularly preferably isopropanol.

This reaction is not possible with the product of the formula (IV), i.e. with the trihydrochloride, without the presence of a base such as, for example, pyridine.

The amount of dimethyl dicarbonate is from 1.0 to 3.0 equivalents, preferably from 1.0 to 2.0 equivalents, based on the compound of the formula (VI) employed.

Possible reaction temperatures are 0-65° C., preferably 15-40° C.

The crude product of the formula (I) precipitates and is isolated by filtration. It is washed with the $C_1$-$C_4$-alcohol and dried under reduced pressure in a customary manner.

In the reaction with dimethyl dicarbonate, the crude product of the formula (I) is obtained directly. Further addition of base is therefore not required.

Both processes, i.e. the reaction of the compound of the formula (VI) with methyl chloroformate and subsequent cleavage of the hydrochloride of the formula (VII) with base or the reaction of the compound of the formula (VI) with dimethyl dicarbonate afford a comparable quality of the crude product of the formula (I), so that the crude product of the formula (I) from the two processes can be used in the same manner for the use as pharmaceutically active compound.

Both processes are preferred according to the invention.

The compound of the formula (I) can form solvates or solvent-containing solid forms, for example methanol-, ethanol-, or isopropanol-containing solid forms. It is therefore possible, that, when the hydrochloride of the formula (VII) is cleaved to the crude product of the formula (I) or when the crude product of the formula (I) is synthesized directly with dimethyl dicarbonate, a solvate of the $C_1$-$C_4$-alcohol used as solvent is obtained. The solvate may be so stable that, during drying of the crude product of the formula (I), it does not decompose completely, and clearly noticeable solvent residues, i.e., for example, of the $C_1$-$C_4$-alcohol in question, thus remain in the crude product. On the other hand, the crude product of the formula (I) must not be dried at temperatures which are too hot, since it may decompose with formation of byproducts at temperatures which are too high.

Accordingly, according to the invention it is preferred to dry the crude product of the formula (I) from the cleavage of the hydrochloride of the formula (VII) with base or from the direct synthesis with dimethyl dicarbonate at a product temperature of not more than 110°, particularly preferably at a product temperature of not more than 100°. Here, it is particularly preferred for any residues of $C_1$-$C_4$-alcohol present as solvate to remain in the crude product of the formula (I) and to use the crude product of the formula (I) in this form for preparing the intermediate of the formula (II). According to the invention, with very particular preference, the crude product of the formula (I) contains isopropanol as residual solvent in a range of from 0 to 13%.

Purification of the Crude Product of the Compound of the Formula (I)

The crude product of the formula (I) obtained in this manner is then purified for use as pharmaceutically active compound. In this purification, the compound of the formula (II) is produced as intermediate.

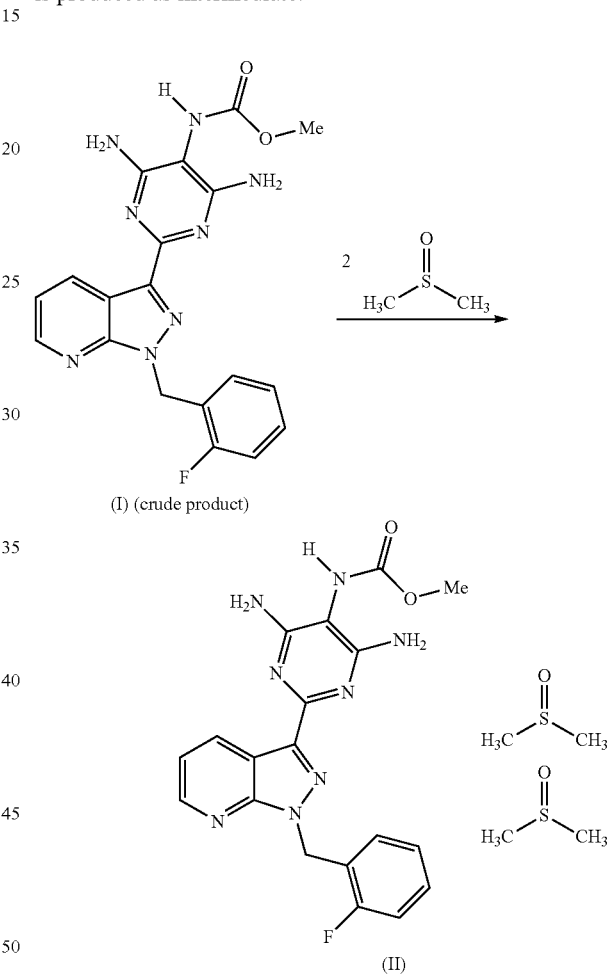

To this end, the crude product of the formula (I) is dissolved in DMSO, if appropriate in the presence of a pharmaceutically acceptable simple solvent from the class of the ketones, ethers, esters or alcohols. Examples of such solvents which may be mentioned are: methanol, ethanol, isopropanol, 1-butanol, 2-butanol, ethyl acetate, isopropyl acetate or propyl acetate, butyl acetate, tert-butyl methyl ether, diisopropyl ether, acetone, methyl ethyl ketone, methyl isobutyl ketone, etc. Preference is given to ethanol, isopropanol, ethyl acetate, isopropyl acetate, butyl acetate, methyl ethyl ketone, methyl isobutyl ketone; particular preference is given to ethyl acetate.

It is also possible to use mixtures of these solvents.

DMSO is added in an amount of from 250 to 750% by weight, preferably from 350 to 600% by weight, based on the amount of the crude product of the formula (I).

If appropriate, activated carbon may be added to this mixture in an amount of from 0.25 to 25% by weight, preferably from 0.5 to 10% by weight, based on the amount of the crude product of the formula (I).

To form a solution, the mixture is heated to 40-120° C., preferably 50-100° C.

To form a pharmaceutically acceptable product, the solution has to be filtered. The filtration has to be carried out independently of whether activated carbon was added or not.

The amount of the pharmaceutically acceptable solvent added prior to the filtration is from 50 to 200% by weight, preferably from 75 to 150% by weight, based on the DMSO.

The filtration is carried out hot, the temperatures are 40-120° C., preferably 50-100° C.

After the filtration, a pharmaceutically acceptable solvent, preferably the same solvent as above, is added to the hot filtrate.

The total amount of solvent added before and after the filtration is from 125 to 300% by weight, preferably 150-250% by weight, based on the DMSO.

The addition temperature is 30-100° C., preferably 35-75° C.

Prior to the isolation of the purified solid of the formula (II), to bring the precipitation to completion, the mixture is cooled to a temperature range of 0-30° C., preferably to an ambient temperature of, for example, 20-25° C.

The isolation is carried out using customary isolation devices such as a nutsche filter or a centrifuge. To remove the mother liquor, the product is, during isolation, washed with a pharmaceutically acceptable solvent, the same solvent as above being preferred. The product of the formula (II) obtained in this manner can now be dried or, alternatively, be used in moist form comprising solvent residues in a boiling step.

After the DMSO redissolution, the product still comprises, even after washing, considerable amounts of DMSO. Depending on how well the product has been washed, the DMSO content is usually from 26 to 35% by weight. In products which have been washed very well, the DMSO content is 27-31% by weight. The remainder to 100% is virtually exclusively the product of the formula (I). Accordingly, the composition of the solid obtained from the DMSO redissolution corresponds to a DMSO disolvate of the compound of the formula (I), i.e. a structure of the formula (II).

According to the invention, when purifying the compound of the formula (I), the DMSO-containing product having the composition of the compound of the formula (II) is particularly preferably isolated as a moist product or in a vacuum-dried form.

The compound of the formula (II) is novel. It can be prepared in pure form as described in the working examples below and be characterized analytically.

For pharmaceutical use, the DMSO has to be removed from the DMSO-containing product of the formula (II).

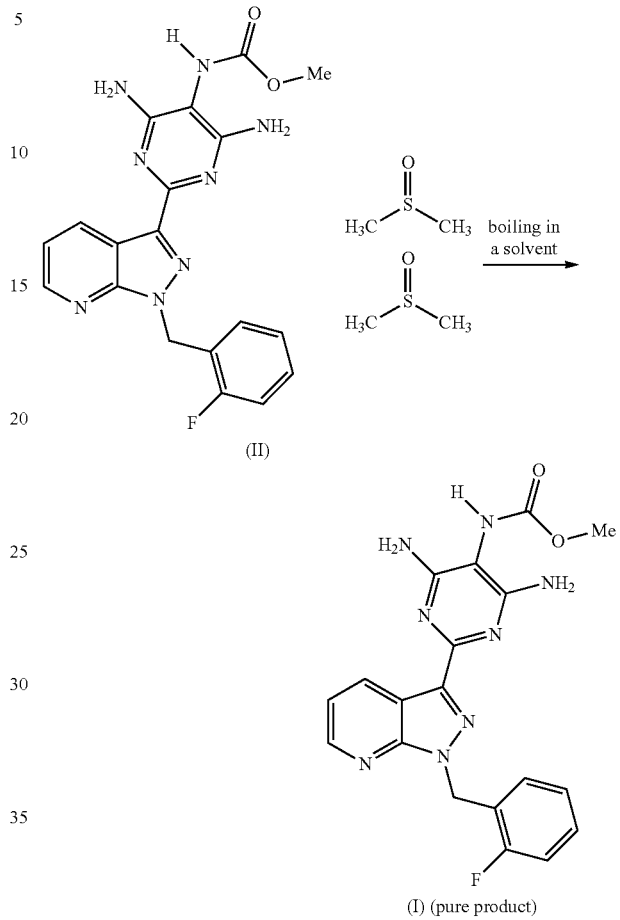

To this end, the product of the formula (II) is dissolved in a pharmaceutically acceptable solvent from the class of the ketones, ethers, esters or alcohols. Examples of such solvents which may be mentioned are: methanol, ethanol, isopropanol, 1-butanol, 2-butanol, ethyl acetate, isopropyl acetate or propyl acetate, butyl acetate, tert-butyl methyl ether, diisopropyl ether, acetone, methyl ethyl ketone, methyl isobutyl ketone, etc. Preference is given to ethanol, isopropanol, ethyl acetate, isopropyl acetate, butyl acetate, methyl ethyl ketone, methyl isobutyl ketone. It is also possible to use mixtures of these solvents. Particular preference is given to ethyl acetate or a mixture of ethyl acetate with ethanol.

Boiling takes place at reflux of the solvent in question or, if appropriate, at slightly elevated pressure. The temperature is 50-150° C., preferably 70-120° C.

The process according to the invention offers marked advantages compared to the prior art. Surprising was in particular that the formation of the compound of the formula (VI) (free base) instead of the compound of the formula (IV) (trihydrochloride) allowed the yield to be increased markedly, with a simultaneous markedly more simple industrial practice (no acid-proof parts of the plant).

The compound of the formula (VI) can then be converted in two novel pyridine-free processes with methyl chloroformate or dimethyl carbonate into the compound of the formula (I). These novel processes are very simple and can be carried out with minimum expense in industry. During the reaction, no pyridine solvent is required and the yields obtained are very high. The product formed is in this case present suspended as a solid and can be isolated without evaporation steps by simple filtration.

It is furthermore surprising that the purification for pharmaceutical use takes place in particular by redissolution in a DMSO-containing solvent and that the novel compound of the formula (II) is obtained as a purified product. By this step, all impurities are removed except for small residual amounts, so that, after the DMSO has been removed by simple boiling, a highly pure solid remains. This solid is generally colourless to very slightly yellow and the analytical purity (HPLC) is markedly above 99% by weight, which is very advantageous for pharmaceutical use.

The process can be carried out safely technically and allows a production on an industrial scale. It can be adapted flexibly to existing apparatus in the plant. In a particularly preferred embodiment, the product isolation is carried out in a nutsche filter dryer, whereby handling of the solid with the associated risk of contamination is avoided.

In a further particularly preferred embodiment, in the purification of the crude product of the formula (I), the intermediate isolation of the product of the formula (II) is carried out in a nutsche filter dryer. Subsequent removal of the DMSO from the product of the formula (II) isolated as an intermediate in the nutsche filter dryer is carried out by direct addition of solvent to the nutsche filter dryer with or without intermediate drying of the product (II). This avoids open handling of the solid of the product (II) with the associated risk of contamination.

EXPERIMENTAL PART

Abbreviations and Acronyms

| abs. | absolute |
|---|---|
| cat. | catalytic |
| CI | chemical ionization (in MS) |
| d | day(s) |
| TLC | thin-layer chromatography |
| DMF | dimethylformamide |
| DMSO | dimethyl sulphoxide |
| ee | enantiomeric excess |
| EI | electron-impact ionization (in MS) |
| ent | enantiomer/enantiomerically pure |
| eq | equivalent(s) |
| ESI | electrospray ionization (in MS) |
| GC-MS | gas chromatography-coupled mass spectrometry |
| % by weight | percent by weight |
| h | hour(s) |
| HPLC | high-pressure, high-performance liquid chromatography |
| conc. | concentrate |
| LC-MS | liquid chromatography-coupled mass spectrometry |
| min | minute(s) |
| MS | mass spectrometry |
| NMR | nuclear magnetic resonance spectrometry |
| Ph | phenyl |
| $R_f$ | retention index (in TLC) |
| $R_t$ | retention time (in HPLC) |
| RT | room temperature |
| v/v | volume-to-volume ratio (of a solution) |
| aq. | aqueous, aqueous solution |

The examples below illustrate the invention, but the invention is not limited to the examples.

Example 1

Preparation of 2-[1-(2-fluorobenzyl)-1H-pyrazolo[3,4-b]pyridin-3-yl]-4,5,6-pyrimidine-triamine (VI)

In a pressure autoclave, 1100 g of the compound of the formula (III) were suspended in 5.4 l of DMF. 44 g of a conventional water-moist (about 50%) 5% Pd/carbon catalyst were added, and the sealed autoclave was, after inertization with nitrogen and application of hydrogen, hydrogenated at a hydrogen pressure of 65 bar and an internal temperature of about 60° C. for about 18 h. After cooling to about 25° C., venting and inertization, the autoclave content was removed, rinsing with 650 ml of DMF.

Three of such reactions carried out in the same manner were combined, the old catalyst was filtered off, the filtercake was rinsed with 1.1 l of DMF and the filtrate was concentrated under reduced pressure to about one third of its mass. Successively, 8.25 l of methanol and 8.25 l of water were metered into the residue of about 6.5 kg, to bring the crystallization to completion, the suspension was cooled to about 5° C. and the solid was filtered off and washed with methanol/water (1:1 vol). The product was dried at 50° C. under reduced pressure. The weight was 2415 g, which corresponds to 91.8% of theory. The content of the target product of the formula (VI) (free base) was >98 area % or >97% by weight. The most significant impurities were DMF (about 0.8% by weight) and water (about 0.5% by weight).

Example 2

Preparation of the crude product of methyl 4,6-diamino-2-[1-(2-fluorobenzyl)-1H-pyrazolo-[3,4-b]pyridin-3-yl]-5-pyrimidinylcarbamate (I)

3063 g of the compound of the formula (VI) and 30.7 l of technical grade isopropanol were initially charged in a reaction vessel. With stirring, 1641 g of dimethyl dicarbonate were metered in at 20-25° C., and the mixture was stirred at this temperature for 22 h. The precipitated product was filtered off with suction, washed with industrial grade isopropanol and dried at 95° C. under reduced pressure. The weight of the product obtained was 3748 g or 105.9% of theory. The crude product of the formula (I) contained, inter alia, about 4.7% of isopropanol virtually unremovable by drying (partially, an isopropanol solvate was present), and the analytical content was 89.5% by weight (HPLC). Based on this content, the yield was 94.8% of theory.

Example 3

Preparation of 2-[1-(2-fluorobenzyl)-1H-pyrazolo[3,4-b]pyridin-3-yl]-4,5,6-pyrimidine-triamine (VI)

In a pressure autoclave, 300 g of the compound of the formula (III), 1600 ml of DMF and 60 g of water-moist Raney nickel were initially charged and, after inertization, hydrogenated at an internal temperature of 60° C. and a hydrogen pressure of 65 bar for 18 h. After cooling and venting, the old catalyst was filtered off and rinsed with 100 ml of DMF. The filtrate was concentrated under reduced pressure to 530 g, and at 35-40° C., 750 ml of methanol and then, after cooling, at 0-5° C., 750 ml of water were metered into the residue. The solid was filtered off and dried at 50° C. under reduced pressure. The weight of solid of the formula (VI) (free base) was 219.7 g or 91.8% of theory.

Example 4

Preparation of the crude product of methyl 4,6-diamino-2-[1-(2-fluorobenzyl)-1H-pyrazolo-[3,4-b]pyridin-3-yl]-5-pyrimidinylcarbamate (I)

In a reaction vessel, 1.50 kg of the compound of the formula (VI) were initially charged in 14.25 l of isopropanol, and the mixture was heated with stirring to 35° C. 531 g of methyl chloroformate were, at a steady rate, metered in over a period of 30 min, rinsing with 750 ml of isopropanol, and the mixture was stirred at 35° C. for 16 h. The mixture was then heated to 50° C. and 3.85 l of methanol and 606 g of triethylamine were metered in with stirring at 50° C., rinsing with 450 ml of methanol. The mixture was then stirred at 50° C. for 1 h, cooled to RT and stirred at RT for 1 h. The suspended solid was filtered off with suction, washed twice with in each case 3.0 l of isopropanol/methanol (4:1) and once with 3.0 l of isopropanol and sucked dry. The moist product was dried at 50° C. for 1 h and then at 100° C. for 22 h in a vacuum drying cabinet. The weight of the product obtained was 1.793 kg or 103.3% of theory. The product of the formula (VI) contained 6.45% of isopropanol virtually unremovable by drying (partially, an isopropanol solvate was present), and the analytical content was 87.9% by weight (HPLC). Based on this content, the yield was 90.8% of theory.

Example 5

Preparation of methyl {4,6-diamino-2-[1-(2-fluorobenzyl)-1H-pyrazolo[3,4-b]pyridin-3-yl]pyrimidin-5-yl}carbamate sulphinyldimethane (1:2) of the formula (II)

1230 g of a crude product of the formula (I) prepared analogously to Example 2 (content 89.1%) were dissolved in 15.0 l of ethyl acetate and 6.6 l of DMSO at reflux (about 85-87° C.), and the hot solution was filtered through a fine-pored filter and slowly, with stirring, allowed to cool to RT and then to 10° C. The precipitated solid was filtered off, washed three times with a total of 1.2 l of ethyl acetate and dried under reduced pressure at 50° C. for 20 h. The weight was 1382 g. Taking into account the content of the compound of the formula (I) employed, this corresponds to 91.2% of theory. The solid contained 27.4% by weight (GC) of DMSO and 72.6% by weight (HPLC) of the compound of the formula (I). Analytically, it thus corresponded to a DMSO bissolvate of the formula (II).

$^1$H-NMR (500 MHz in DMF-$d_7$):

d=2.58 (s, 12H, 4 $CH_3$ at DMSO), 3.65 (s, 3H, O—$CH_3$), 5.89 (s, 2H, —$CH_2$—), 6.33 (s, 4H, 2-$NH_2$), 7.05-7.39 (m, 5H, 4 aromatic H at the o-fluorobenzyl substituent and 1H at the pyrido ring meta to the pyrido nitrogen), 8.0 (s, 1H, —NH—), 8.60 (dd, 1H, at the pyrido ring ortho to the pyrido nitrogen), 9.13 (dd, 1H, at the pyrido ring para to the pyrido nitrogen).

Elemental analysis:

| found | C: 49.4% | calculated | C: 48.92% |
|---|---|---|---|
| | H: 5.2% | | H: 5.18% |
| | N: 20.0% | | N: 19.84% |

Example 6

Preparation of pure pharmaceutically acceptable methyl 4,6-diamino-2-[1-(2-fluorobenzyl)-1H-pyrazolo[3,4-b]pyridin-3-yl]-5-pyrimidinylcarbamate (I)

7.1 kg of the product of the formula (II) were suspended in 171.6 kg of ethyl acetate and 42 kg of ethanol, and the mixture was stirred at reflux (internal temperature about 73-74° C.) for 20 h. The suspension was cooled to RT and filtered off with suction, and the product was washed four times with in each case 12.2 kg of ethyl acetate. The product was then washed twice with in each case 12.2 kg of water to expel the ethyl acetate, and the moist product was dried under reduced pressure at 50° C. until its mass remained constant. The yield of pure product of the formula (I) was 4.3 kg or 84% of theory. The content of the product was more than 99% (HPLC).

The invention claimed is:

1. A process for purifying methyl {4,6-diamino-2-[1-(2-fluorobenzyl)-1H-pyrazolo[3,4-b]pyridin-3-yl]pyrimidin-5-yl}carbamate, characterized in that the crude methyl {4,6-diamino-2-[1-(2-fluorobenzyl)-1H-pyrazolo[3,4-b]pyridin-3-yl]pyrimidin-5-yl}carbamate is dissolved in dimethyl sulphoxide and the resulting methyl {4,6-diamino-2-[1-(2-fluorobenzyl)-1H-pyrazolo[3,4-b]pyridin-3-yl]pyrimidin-5-yl}carbamate sulphinyldimethane (1:2) is isolated and the dimethyl sulphoxide is removed by boiling in a pharmaceutically acceptable solvent.

2. The compound methyl {4,6-diamino-2-[1-(2-fluorobenzyl)-1H-pyrazolo[3,4-b]pyridin-3-yl]pyrimidin-5-yl}carbamate sulphinyldimethane (1:2) of the formula

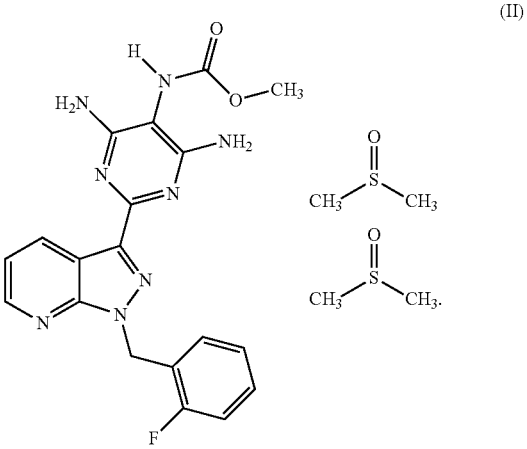

(II)

* * * * *